United States Patent [19]

Drauz et al.

[11] Patent Number: 4,618,730
[45] Date of Patent: * Oct. 21, 1986

[54] PROCESS FOR THE PRODUCTION OF PYROCATECHOL AND HYDROQUINONE

[75] Inventors: Karlheinz Drauz, Freigericht; Axel Kleemann, Hanau, both of Fed. Rep. of Germany

[73] Assignee: Degussa Aktiengesellschaft, Frankfurt, Fed. Rep. of Germany

[*] Notice: The portion of the term of this patent subsequent to Aug. 6, 2002 has been disclaimed.

[21] Appl. No.: 587,652

[22] Filed: Mar. 8, 1984

[30] Foreign Application Priority Data

Mar. 11, 1983 [DE] Fed. Rep. of Germany ....... 3308737

[51] Int. Cl.$^4$ ..................... C07C 37/60; C07C 39/10
[52] U.S. Cl. .................... 568/771; 568/741; 568/800; 568/803
[58] Field of Search ............... 568/803, 771, 798, 800, 568/741, 763

[56] References Cited

U.S. PATENT DOCUMENTS 3,943,179  3/1976  Bost et al. ........................ 568/771
4,533,766  8/1985  Drauz et al. ..................... 568/771

FOREIGN PATENT DOCUMENTS 7312990  4/1974  Netherlands ..................... 568/771

OTHER PUBLICATIONS

Schmidt, Z. fur Anorganische und Allgemeim Chemie, vol. 331, pp. 92–97 (1964).
Holleman et al, Lehrbuch Des Anorganischen Chemie, pp. 180, 195 (1955).

*Primary Examiner*—Werren B. Lone
*Attorney, Agent, or Firm*—Cushman, Darby & Cushman

[57] ABSTRACT

The known nuclear hydroxylation of phenol with organic solutions of hydrogen peroxide in the presence of a catalyst is carried out in improved manner by employing both (1) a special, practically water free solution of hydrogen peroxide in an organic solvent which forms an azeotrope with water, which azeotrope boils below the boiling point of hydrogen peroxide, and (2) sulfur dioxide as a catalyst. Through this, the nuclear hydroxylation is substantially simpler than previously; difficult separations, e.g., from water-phenol, or the separation and recovery of the catalyst are eliminated. Besides, the yields are increased.

32 Claims, No Drawings

PROCESS FOR THE PRODUCTION OF PYROCATECHOL AND HYDROQUINONE

BACKGROUND OF THE INVENTION

The invention is directed to the production of pyrocatechol and hydroquinone by nuclear hydroxylation of phenol with hydrogen peroxide.

Pyrocatechol and hydroquinone are derivatives of phenol. They are employed in the production of dyestuffs, in the production of synthetic resins, in photography, and for the production of important plant protectives.

Their production, as is the case with polyhydric phenols in general, therefore, has long been the object of thorough investigations. The hydroxylation has been carried out both with hydrogen peroxide itself as well as with hydroperoxides, peroxides, or even per acids such as, e.g., performic acid or peracetic acid.

Nevertheless, hydrogen peroxide was preferred since it is the most readily available and since with percarboxylic acids, hydroperoxides and peroxides side reactions occur (European published application No. 0027593).

There was always present a catalyst in these hydroxylations. This catalyst can be a metalloid such as sulfur, selenium, tellurium, phosphorus, arsenic, or antimony in elemental form (German OS No. 2348957) or there can be used boron compounds (German Pat. No. 1543830).

Various processes operate with transition elements in the form of their ions (German OS No. 2162552), especially with iron ions (German OS No. 2162589 or German Pat. No. 2407398) or cobalt ions (German AS No. 2341743), or even with the corresponding oxides (Milas U.S. Pat. No. 2,395,638).

Besides, there are employed strong acids such as sulfuric acid, sulfonic acids (German OS No. 2138735, German AS No. 2410742, German AS No. 2410758, German AS No. 2462967), or a mixture of sulfuric acid and phosphoric acid (German OS No. 2138735), there are also mentioned in the last named published application organic acids such as, inter alia, trichloroacetic acid or tartaric acid.

The already mentioned percarboxylic acids likewise serve as catalysts (French Pat. No. 1479354). In all of the mentioned catalysts, it is a matter with the catalysts being solid or liquid materials. Hydrogen peroxide, as preferred oxidation agent, for the most part is employed in aqueous solutions of various concentrations up to very high concentrations which have the danger of explosion; thus, the process according to German Pat. No. 2064497 operates with solutions which only contain 5 weight water, but even at this highly concentrated hydrogen peroxide the yield of dihydroxy derivatives was only 70% and was reduced considerably corresponding to the dilution of the hydrogen peroxide.

Additionally, in these and also in other processes, the operation must be carried out with a very large excess of the phenol to be hydroxylated in order in general to obtain the above-stated yield. If this excess is reduced, e.g., from 20 moles to 10 moles per mole of hydrogen peroxide, then the yield is reduced drastically despite the higher concentration of hydrogen peroxide.

However, as is known, this type of excess of a reactant, which must be recycled, requires additional industrial expense; above all in regard to the size of the apparatus employed.

Since care is always taken to avoid large excesses of one component as far as possible, there have been attempts to avoid employing aqueous solutions of hydrogen peroxide.

Thus, different solutions of hydrogen peroxide in organic solvents have already been used. For example, according to the process of German Pat. No. 2410758, there are preferably employed hydrogen peroxide solutions in derivatives of phosphoric acid or phosphonic acid, namely in the presence of a strong acid, such as sulfuric acid (100%) or fluorosulfonic acid.

However, these highly concentrated strong acids have the disadvantage that their separation from the reaction mixture creates difficulties (German AS No. 2658943), above all since their concentration in the reaction mixture has a considerable influence on the length of the reaction.

The excess of phenol was indeed reduced somewhat in contrast to this in the process of German AS No. 2064497, but this did not outweigh the disadvantage of the strong acids.

An additional difficulty in the process of German Pat. No. 2410758 in the working up of the reaction mixture was produced by the presence of the water formed after the reaction with hydrogen peroxide.

Since the solvent for hydrogen peroxide employed in part is higher boiling than the phenol employed and this forms an azeotrope with water whose boiling point is below that of the organic solvent, it was highly problematic that a troublefree separation of the phenol from the reaction mixture could be attained.

Therefore, other ways were tried, first to manage without catalyst, i.e., above all without the strong acids. Since the catalysts above all were needed for the activation of hydrogen peroxide, the process of German AS No. 2658943 was operated with organic solutions o peracetic acid. An additional catalyst was not used.

Entirely apart from the fact that the mentioned process presupposes a complete plant for the production of an organic percarboxylic acid, which first is obtained from hydrogen peroxide and carboxylic acid, and thereupon is produced by extraction of this so-called "equilibrium acid" from its aqueous solution, it has been shown a stated good selectivity and good yield was only possible in the presence of additional peracid stabilizers (German OS No. 2364181; European OS No. 0027593). Also, the attempt to produce pyrocatechol and hydroquinone without catalyst with gaseous hydrogen peroxide could be carried out only poorly on an industrial scale because of the danger of explosion (Japan published application No. 24056/1974).

From what has been said above, the result is that processes in which hydrogen peroxide is used as the most readily accessible hydroxylating agent do not make possible any entirely satisfactory process for the industrial production of dihydroxybenzenes.

Therefore, in recent times, there have only been developed processes which do not directly use hydrogen peroxide and in part for this reason require high industrial expense.

The subject matter of the invention, therefore, is carrying out the nucelar hydroxylation of phenol with hydrogen peroxide in the presence of catalysts in an industrially simple manner and with very good yields.

SUMMARY OF THE INVENTION

It has now been found that this problem can be solved by employing an organic solution of hydrogen peroxide if the reaction is carried out in the presence of sulfur dioxide and with a water-free solution of hydrogen peroxide, which preferably has a water content below 0.5 weight %, e.g., 0%, and which is produced with an organic solvent which forms an azeotrope with water, which azeotrope has a boiling point below the boiling point of hydrogen peroxide, referred to normal pressure. As "water free" there is intended solutions which at most have up to 1 weight % of water.

As solvents, there can be used ethers such as dioxane, diisopropyl ether, methyl tert. butyl ether.

Preferred solvents are alkyl or cycloalkyl esters of saturated aliphatic carboxylic acids which contain 4-8 carbon atoms, e.g., alkyl alkanoates.

Especially suitable esters are those of acetic acid and propionic acid, above all n-propyl acetate or isopropyl acetate.

Other suitable esters include ethyl acetate, hexyl acetate, butyl acetate, sec. butyl acetate, amyl acetate, cyclohexyl acetate, cyclopentyl acetate, methyl propionate, ethyl propionate, propyl propionate, isopropyl propionate, butyl propionate, methyl butyrate, ethyl butyrate, n-propyl butyrate, ethyl valerate, ethyl hexanoate.

There can also be used mixtures of esters.

The organic hydrogen peroxide solutions can be stabilized in customary manner, see Ullmann, Enzyklopadie der technischen Chemie, 4th Edition, Vol. 17, page 709, the entire disclosure of which is hereby incorporated by reference and relied upon.

The mentioned solutions of hydrogen peroxide in alkyl or cycloalkyl esters are obtained according to the process of German OS No. 3225307.9, the entire disclosure of which is hereby incorporated by reference and relied upon.

The sulfur dioxide acting as catalyst can be used in the gaseous form. Sulfur dioxide, however, can also be dissolved in a solvent at pleasure, which does not enter into a disturbing reaction with sulfur dioxide or with hydrogen peroxide, for example in dialkyl ethers, e.g., dipropyl ether, diisopropyl ether or dibutyl ether, esters of phosphoric acid or phosphonic acid, e.g., trioctyl phosphate, tributyl phosphate, diethyl phthalate, diethyl methane phosphonate, dibutyl ethane phosphonate, etc. The concentration depends on the solubility of $SO_2$ in the solvent. Generally, it is between 0.1 and 50, preferably 1 to 10 weight %. However, it is favorable to employ sulfur dioxide as a solution in one of the above described carboxylic acid esters. Sulfur dioxide is used in very small amounts, i.e., in amount of 0.0001 to 0.1 mole, preferably from 0.0005 to 0.01 mole based on 1 mole of hydrogen peroxide, above all compared with hydroxylations catalyzed by protonic acids on the acid side.

The reaction generally occurs at 20° to 200° C., preferably at a temperature of 40° to 180° C.

The organic solution of hydrogen peroxide in the mentioned alkyl or cycloalkyl esters makes possible higher concentrations (up to 60 weight %) and are characterized by very low water content (below 0.5 weight %), see German OS No. 3225307.9.

As stated, the process of the invention permits the nuclear hydroxylation of phenol.

The pressure is not critical for the reaction. Generally, the reaction is carried out at normal pressure.

The duration of the reaction depends on the temperature and the concentration of the sulfur dioxide.

In order to establish the best reaction time, there can be carried out a small-scale experiment.

Preferably, the procedure is such that after 15 minutes more than 95% of the hydrogen peroxide employed is reacted.

The hydroxylation of phenol according to the process of the invention is especially successful if water-free solutions of hydrogen peroxide in the mentioned carboxylic acid esters are employed with a weight ratio of about 1:4 to 2:1 $H_2O_2$/carboxylic acid ester.

This weight ratio is also attained in using less concentrated $H_2O_2$ solutions by distilling off overhead from these solutions the carboxylic acid ester which is mixed with the phenol. The removal of the ester can be controlled by any desired value.

The distillation is carried out in such manner that practically no phenol and no hydrogen peroxide is carried out with the carboxylic acid ester.

The preparation of the reaction mixture is substantially simpler than the methods previously known. An azeotropic dehydration of the phenol takes place as a positive secondary effect, because the azeotrope water/carboxylic acid ester is the component which has the lowest boiling point. Since the ester used as solvent according to the invention boils lower than the phenols which are converted, first there is distilled off an azeotrope between the ester and the water. The difficulties of a water-phenol separation, such as previously occurred, are eliminated. This is especially important since phenol is used in excess and must be returned again.

In the preparation, it is not absolutely necessary, because of the extremely low catalyst concentrations, to carry out a separation of the catalyst, for example, by neutralization, before a distillative separation. The crude reaction mixture is subjected directly to a distillation.

The molar ratio of phenol and hydrogen peroxide is between 5 to 20:1, preferably 5 to 15:1, very favorably at 7 to 15:1.

In the process of the invention, it is true that a catalyst is employed. However, it is used in such a slight amount that a special separation of it before the distillative working up of the reaction mixture is superfluous.

Additionally, there is produced a very favorable space-time-yield because of the short reaction times. Thus, for the industrial carrying out of the operation, small reaction volumes are sufficient. Thus, there are present 99% or more conversion after only 20 to 30 minutes.

Besides through the short duration of the reaction, there is simultaneously reduced the possible danger of decompositions. This reaction also can be readily carried out continuously.

Furthermore, it is substantial that the volatile solvent together with the water present can be separated from the residual phenol and the reaction products without trouble so that the phenol can be returned into the reaction step again in practically water-free condition.

All of these advantages are not tied to a reduction of the yields obtained according to the previous state of the art, but instead the yields are even increased.

Unless otherwise indicted, all parts and percentages are by weight.

The process can comprise, consist essentially of, or consist of the stated steps with the recited materials.

The invention is explained in more detail in connection with the following examples.

DETAILED DESCRIPTION

Example 1

94.1 grams (1.0 mole) of phenol were heated to 100° C. There were added to the stirred melt 0.4 grams of a 4.8 weight % solution of sulfur dioxide in n-propyl acetate and subsequently 6.37 grams of a 53.4 weight % water-free solution of hydrogen peroxide in n-propyl acetate (=0.1 mole). The temperature in the reaction solution increased after that to 154° C. After the exotherm died down, there was determined after 10 minutes a hydrogen peroxide reaction of 98.3%. The reaction mixture then contained 3.15 grams (28.6 mmoles) of hydroquinone, and 6.47 grams (58.7 mmoles) of pyrocatechol, which corresponds to a total yield of dihydroxybenzenes of 88.9% based on the hydrogen peroxide reacted.

Example 2

141 grams (1.5 moles) of phenol were heated to 100° C. There were added to the stirred melt 0.4 grams of a 4.8 weight % solution of sulfur dioxide in n-propyl acetate and subsequently 6.37 grams of a 53.4 weight % water-free solution of hydrogen peroxide in n-propyl acetate (0.1 mole). The temperature in the reaction solution increased after that to 126° C. After the exotherm died down, there was ascertained after twenty minutes a hydrogen peroxide reaction of 90.4%. The reaction mixture then contained 3.05 grams (27.7 mmoles) of hydroquinone, and 6.15 grams (55.8 mmoles) of pyrocatechol, which corresponds to a total yield of dihydroxybenzenes of 92.4%, based on the $H_2O_2$ reacted.

Example 3

65.9 grams (0.7 mole) of phenol were heated to 100° C. There were added to the stirred melt 0.27 gram of a 4.8 weight % solution of sulfur dioxide in n-propyl acetate and subsequently 6.37 grams of a 53.4 weight % water-free solution of hydrogen peroxide in n-propyl acetate (0.1 mole). The temperature in the reaction mixture increased after that to 152° C. After the exotherm died down, after five minutes there was established a hydrogen peroxide reaction of 91.4%. The reaction mixture then contained 2.86 grams (25.9 mmoles) of hydroquinone and 5.35 grams (48.6 mmoles) of pyrocatechol, which corresponds to a total yield of dihydroxybenzenes of 81.6%, based on the hydrogen peroxide reacted.

Example 4

94.1 grams (1.0 mole) of phenol were heated to 100° C. There were added to the stirred melt 0.4 gram of a 4.8 weight % solution of sulfur dioxide in n-propyl acetate and subsequently 5.4 grams of a 63 weight % water-free solution of hydrogen peroxide (0.1 mole) in ethyl acetate. The temperature increased to 152° C. After the exotherm died down, there was determined after five minutes a hydrogen peroxide reaction of 96.7%. The reaction mixture then contained 2.82 grams (25.6 mmoles) of hydroquinone and 5.87 grams (53.3 mmoles) of pyrocatechol, which corresponds to a total yield of dihydroxybenzenes of 81.6% based on the hydrogen peroxide reacted.

Example 5

94.1 grams (1.0 mole) of phenol were heated to 100° C. There were added to the stirred melt 0.4 gram of a 4.8 weight % solution of sulfur dioxide in n-propyl acetate and subsequently 5.7 grams of 59.6 weight % water-free solution of hydrogen peroxide (0.1 mole) in methyl propionate. The temperature increased to 151° C. After the exotherm died down, there was established after ten minutes a hydrogen peroxide reaction of 98.5%. The reaction mixture then contained 2.95 grams (26.8 mmoles) of hyroquinone and 6.15 grams (55.8 mmoles) of pyrocatechol, which corresponds to a total yield of dihydroxybenzenes of 83.9% based on the hydrogen peroxide reacted.

Example 6

94.1 grams (1.0 mole) of phenol were heated to 100° C. There were added to the stirred melt 0.4 gram of a 4.8 weight % solution of sulfur dioxide in n-propyl acetate and subsequently 11.5 grams of a 29.5 weight % water-free solution of hydrogen peroxide in methyl propionate (0.1 mole). The temperature increased to 146° C. After the exotherm died down, there was ascertained after five minutes a hydrogen peroxide reaction of 95.7%. The reaction mixture then contained 2.94 grams (26.7 mmoles) of hydroquinone and 5.97 grams (54.2 mmoles) of pyrocatechol, which corresponds to a total yield of dihydroxybenzenes of 84.5% based on the hydrogen peroxide reacted.

Example 7

94.1 grams (1.0 mole) of phenol were heated to 100° C. There were added to the stirred melt 0.4 gram of a 4.8 weight % solution of sulfur dioxide in n-propyl acetate and subsequently 7.4 grams of a 46.1 weight % water-free solution of hydrogen peroxide in ethyl propionate (0.1 mole). The temperature increased to 153° C. After the exotherm died down, there was ascertained after twenty minutes a hydrogen peroxide reaction of 99.4%. The reaction mixture then contained 2.65 grams (24.1 mmoles) of hydroquinone and 5.63 grams (51.1 mmoles) of pyrocatechol, which corresponds to a total yield of 75.6% based on the hydrogen peroxide reacted.

Example 8

In a comparison example to Example 2, but which did not follow the process of the invention:

141 grams (1.5 moles) of phenol were heated to 110° C. There were added to the stirred melt 0.02 grams of a 100% sulfuric acid and subsequently 6.37 grams of a 53.4 weight % water-free solution of hydrogen peroxide in propyl acetate (0.1 mole). The temperature increased to 135° C. After the exotherm died down, there was ascertained after 60 minutes a hydrogen peroxide reaction of 99.4%. The reaction mixture contained 1.61 grams (14.6 mmoles) of hydroquinone and 4.34 grams (39.4 mmoles) of pyrocatechol, which corresponds to a total yield of dihydroxybenzenes of 54.4% based on the hydrogen peroxide.

The entire disclosure of German priority application No. P.3308737.7 is hereby incorporated by reference.

Example 9 188,2 grams (2.0 mole) of phenol were heated to 100° C. There were added to the stirred melt 40 ml of sulfur-dioxide-gas (~0.018 mole) and subsequently 19.4 grams of a 35.0 weight % waterfree solution of hydrogen peroxide in isopropyl acetate (0.2 mole). The temperature increased to 153° C. After the exotherm died down, there was ascertained after five minutes a hydrogen peroxide reaction of 97.6%. The reaction mixture then contained 5.8 grams (26.3 mmoles) of hydroquinone and 11.87 grams (53.9 mmoles) of pyrocatechol, which corresponds to a total yield of dihydroxybenzenes of 82.2%, based on hydrogen peroxide reacted.

What is claimed is:

1. A process for the production of pyrocatechol and hydroquinone by nuclear hydroxylation of phenol with hydrogen peroxide in a substantially water-free organic solvent in the presence of a catalyst comprising reacting phenol with hydrogen peroxide in a solution in substantially water-free organic solvent which solvent forms an azeotrope with water, the boiling point of the azeotrope being below the boiling point of hydrogen peroxide, based on normal pressure, said reaction being carried out in the presence of sulfur dioxide as a catalyst.

2. A process according to claim 1 wherein the water content of the solvent is below 0.5%.

3. A process according to claim 2 wherein the water content of the solvent is 0.1 percent by weight.

4. A process according to claim 1 wherein the solvent is an ether or an alkyl or cycloalkyl ester of a saturated, aliphatic carboxylic acid, which ester contains a total of 4–8 carbon atoms.

5. A process according to claim 4 wherein the solvent is an alkyl or cycloalkyl ester of a saturated aliphatic carboxylic acid, which ester contains a total of 4–8 carbon atoms.

6. A process according to claim 5 wherein the solvent is an alkyl alkanoate.

7. A process according to claim 4 wherein the solvent is an ester of acetic acid or propionic acid.

8. A process according to claim 7 wherein the hydrogen peroxide is employed as a solution in n-propyl acetate or isopropyl acetate.

9. A process according to claim 8 wherein the sulfur dioxide is added as a solution in an alkyl or cycloalkyl ester of a saturated, aliphatic carboxylic acid, which ester contains a total of 4–8 carbon atoms.

10. A process according to claim 7 wherein the sulfur dioxide is added as a solution in an alkyl or cycloalkyl ester of a saturated, aliphatic carboxylic acid, which ester contains a total of 4–8 carbon atoms.

11. A process according to claim 4 wherein the sulfur dioxide is added as a solution in an alkyl or cycloalkyl ester of a saturated, aliphatic carboxylic acid, which ester contains a total of 4–8 carbon atoms.

12. A process according to claim 1 wherein the $SO_2$ is added in gaseous form.

13. A process according to claim 12 wherein there is employed sulfur dioxide in an amount of 0.0001 to 0.1 mole per mole of hydrogen peroxide.

14. A process according to claim 11 wherein there is employed sulfur dioxide in an amount of 0.0001 to 0.1 mole per mole of hydrogen peroxide.

15. A process according to claim 10 wherein there is employed sulfur dioxide in an amount of 0.0001 to 0.1 mole per mole of hydrogen peroxide.

16. A process according to claim 9 wherein there is employed sulfur dioxide in an amount of 0.0001 to 0.1 mole per mole of hydrogen peroxide.

17. A process according to claim 8 wherein there is employed sulfur dioxide in an amount of 0.0001 to 0.1 mole per mole of hydrogen peroxide.

18. A process according to claim 7 wherein there is employed sulfur dioxide in an amount of 0.0001 to 0.1 mole per mole of hydrogen peroxide.

19. A process according to claim 5 wherein there is employed sulfur dioxide in an amount of 0.0001 to 0.1 mole per mole of hydrogen peroxide.

20. A process according to claim 1 wherein there is employed sulfur dioxide in an amount of 0.0001 to 0.1 mole per mole of hydrogen peroxide.

21. A process according to claim 20 wherein there is employed 0.0005 to 0.01 mole of sulfur dioxide per mole of hydrogen peroxide.

22. A process according to claim 19 wherein there is employed 0.0005 to 0.01 mole of sulfur dioxide per mole of hydrogen peroxide.

23. A process according to claim 18 wherein there is employed 0.0005 to 0.01 mole of sulfur dioxide per mole of hydrogen peroxide.

24. A process according to claim 17 wherein there is employed 0.0005 to 0.01 mole of sulfur dioxide per mole of hydrogen peroxide.

25. A process according to claim 16 wherein there is employed 0.0005 to 0.01 mole of sulfur dioxide per mole of hydrogen peroxide.

26. A process according to claim 18 wherein the molar ratio of phenol to hydrogen peroxide is from 7 to 15:1.

27. A process according to claim 20 wherein the molar ratio of phenol to hydrogen peroxide is from 5 to 20:1.

28. A process according to claim 1 wherein the temperature is 20° to 200° C.

29. A process according to claim 28 wherein the temperature is 40° to 180° C.

30. A process according to claim 28 wherein the water content of the solvent is below 0.5% and the solvent is an ether or an alkyl or cycloalkyl ester of a saturated aliphatic carboxylic acid, which ester contains a total of 4–8 carbon atoms.

31. A process according to claim 30 wherein the solvent is an alkyl or cycloalkyl ester of a saturated aliphatic carboxylic acid, which ester contains a total of 4–8 carbon atoms.

32. A process according to claim 30 wherein the materials employed consist essentially of phenol, hydrogen peroxide, and the solvent.

* * * * *